US009669145B2

(12) United States Patent
Günther et al.

(10) Patent No.: US 9,669,145 B2
(45) Date of Patent: *Jun. 6, 2017

(54) DEVICE AND METHOD FOR TREATING A MEDICAL FLUID AND MEDICAL CASSETTE

(71) Applicant: Fresenius Medical Care Deutschland GmbH, Bad Homburg (DE)

(72) Inventors: Götz Günther, Bad Homburg (DE); Jürgen Häcker, Neu-Anspach (DE); Markus Köhler, Oberursel (DE); Martin Lauer, St. Wendel (DE); Ralf Müller, Oberursel (DE); Hans-Peter Schneider, Neu-Anspach (DE); Tobias Weber, St. Wendel (DE); Manfred Weis, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 517 days.

This patent is subject to a terminal disclaimer.

(21) Appl. No.: 13/925,571

(22) Filed: Jun. 24, 2013

(65) Prior Publication Data

US 2014/0034557 A1 Feb. 6, 2014

Related U.S. Application Data

(63) Continuation of application No. 12/733,592, filed as application No. PCT/EP2008/003978 on May 16, 2008, now Pat. No. 8,470,171.

(30) Foreign Application Priority Data

Sep. 10, 2007 (DE) ........................ 10 2007 042 964

(51) Int. Cl.
*A61M 1/14* (2006.01)
*A61M 1/16* (2006.01)
*A61M 1/28* (2006.01)

(52) U.S. Cl.
CPC ................ *A61M 1/14* (2013.01); *A61M 1/16* (2013.01); *A61M 1/28* (2013.01); *A61M 2205/122* (2013.01); *Y10T 29/49826* (2015.01)

(58) Field of Classification Search
CPC .... A61M 1/16; A61M 1/28; A61M 2205/122; Y10T 29/49826
See application file for complete search history.

(56) References Cited

U.S. PATENT DOCUMENTS 5,421,823 A 6/1995 Kamen et al.
6,542,761 B1 4/2003 Jahn et al.
(Continued)

FOREIGN PATENT DOCUMENTS

CN 1658916 8/2005
DE 10124750 11/2002
(Continued)

OTHER PUBLICATIONS

English translation of Japanese Patent Application No. 2003-318143 A (Nov. 2003).*

*Primary Examiner* — John Kim
(74) *Attorney, Agent, or Firm* — Jacobson Holman, PLLC.

(57) ABSTRACT

An apparatus for treating a medical fluid is provided which includes a treatment machine having a coupling surface, with a cassette made of a hard part having liquid-conducting passages which are covered by a flexible film being able to be coupled to the coupling surface of the treatment machine. A corresponding medical cassette is also provided. An air-free coupling of the flexible film of the cassette to the treatment machine is ensured in that air can be sucked out (Continued)

areally along a plane between the flexible film and the coupling surface during the coupling process and/or with a coupled cassette. A method for coupling the cassette and a method for checking the leaktightness of the cassette via the vacuum control of the air suction is also provided.

35 Claims, 5 Drawing Sheets

(56) References Cited

U.S. PATENT DOCUMENTS

| | | |
|---|---|---|
| 6,883,491 B2 | 4/2005 | Arndt et al. |
| 7,648,627 B2 | 1/2010 | Beden et al. |
| 2003/0100882 A1 | 5/2003 | Beden et al. |
| 2005/0126998 A1 | 6/2005 | Childers |
| 2007/0112297 A1 | 5/2007 | Plahey et al. |
| 2012/0181225 A1 | 7/2012 | Weis |
| 2013/0118970 A1 | 5/2013 | Beden et al. |
| 2015/0165105 A1 | 6/2015 | Beden et al. |

FOREIGN PATENT DOCUMENTS

| | | |
|---|---|---|
| DE | 10157924 | 6/2003 |
| DE | 10224750 | 12/2003 |
| EP | 0980686 | 2/2000 |
| JP | H07-506520 | 7/1995 |
| JP | 09-066495 | 3/1997 |
| JP | 2000-060965 | 2/2000 |
| JP | 2000241501 | 9/2000 |
| JP | 2003-180834 | 7/2003 |
| JP | 2003-318143 | 11/2003 |
| JP | 2005-528168 | 9/2005 |
| WO | WO 03/099355 | 12/2003 |
| WO | WO 2009/006500 | 1/2009 |

* cited by examiner

DEVICE AND METHOD FOR TREATING A MEDICAL FLUID AND MEDICAL CASSETTE

This is a continuation of U.S. patent application Ser. No. 12/733,592, filed Mar. 10, 2010, and issuing as U.S. Pat. No. 8,470,171 on Jun. 25, 2013, which is a national stage of PCT/EP08/003,978 filed May 16, 2008 and published in German, which claims the priority of DE No. 10 2007 042 964.0, filed Sep. 10, 2007, and hereby claims the priorities thereof to which it is entitled.

BACKGROUND OF THE INVENTION

1. Field of the Invention

The present invention relates to an apparatus for treating a medical liquid which includes a treatment machine having a coupling surface, with a cassette made of a hart part having liquid-conducting passages which are covered by a flexible film being able to be coupled to the coupling surface of the treatment machine. The present invention further relates to a medical cassette made of a hard part having liquid-conducting passages which are covered by a flexible film, with the cassette being able to be coupled to the coupling surface of the treatment machine. The present invention further relates to an apparatus for treating a medical liquid which includes a treatment machine having a coupling surface, with a cassette made of a hard part having liquid-conducting passages which are covered by a flexible film. The present invention further relates to a method for coupling a cassette made of a hard part having liquid-conducting passages which are covered by a flexible film to the coupling surface of a treatment machine for the treatment of a medical liquid as well as to a method for checking the leaktightness of such a medical cassette.

2. Description of the Related Art

The treatment machine can be a blood treatment machine such as is used in hemodialysis or in peritoneal dialysis. In such a use, the medical cassette includes the blood-conducting or dialysis liquid-conducting passages and is in communication with actuators and sensors of the treatment machine via the coupling surface. The medical cassette can thus be configured as a cost-effective disposable part, whereas the actuators for the control of the liquid flow through the cassette and the sensors are integrated into the treatment machine for the level detection or for the pressure measurement.

Such medical cassettes configured as disposable articles comprise in this connection a thin-walled three-dimensional hard plastic part having a planar peripheral contact edge and various recesses (chambers, webs and passages). Medical liquids such as dialysate or blood can now be conducted in the chambers and passages formed by these three-dimensional structures of the hard plastic part. The contact plane of the cassette is closed in a liquid tight manner by a flexible film, advantageously a polymer film which is peripherally connected, in particular welded and/or adhesively bonded, to the contact edge of the hard part. The medical cassette is pressed onto the coupling surface of the treatment machine in use with the flexible film so that actuators and sensors of the treatment machine lie on the polymer film. In addition, the flexible film is pressed together with the webs of the cassette by this pressing and thus provides a fluid tight separation of the liquid-conducting passages in the hard part by the webs and the flexible film.

The coupling surface of the treatment machine accordingly usually has actuators, sensors and pressing force transmission surfaces. The actuators and sensors of the blood treatment machine are arranged in this context in the coupled state of the cassette opposite the liquid-conducting passages of the cassette. The actuators can hereby form valves by the pressing down of the film in that the flexible film is pressed into regions of the liquid-conducting passages and closes them. The sensors, for example, measure the pressure or temperature of the liquid located in the liquid-conducting passages. The pressing force transmission surfaces press the flexible film against sealing webs of the hard parts which surround the liquid-conducting passages to seal them with respect to one another and toward the rest of the cassette. In this connection, the coupling surface is usually formed by a planar surface of a support member which is made from metal, for example, with receivers for the sensors and the actuators being provided in the surface, and by the sensors inserted into these receivers in planar fashion.

A flexible mat made, for example, of silicone or another elastomeric material, is usually arranged on the coupling surface of the treatment machine. This has the advantage that the sensor surfaces are protected against environmental influences and the machine surface is moreover liquid tight and thus may ideally be hygienically cleaned. The flexible mat in this context represents a part of the treatment machine to which the cassette is coupled as a disposable part. The operation of the actuators is ensured by the flexibility of the mat. In addition, the flexible film can be pressed well to the coupling surface via the flexible mat, which permits a good contact with the actuators, sensors and pressing force transmission surfaces. The treatment machine can, however, also be operated without a flexible mat so that the flexible film lies directly on the coupling surface and the sensors and actuators couple directly to the film.

There is, however, the difficulty with known systems in the coupling of sensors to the film surface of achieving a good coupling to obtain correct measured values. In particular, air which is trapped in the transmission path between the flexible film and the sensor surface on the insertion of the cassette, produces a falsification of the measured results. This applies to pressure sensors (in particular on the measurement of pressures which are less than the environmental pressure), but also in level detection and likewise to actuators such as valves. Unwanted air inclusions between the outer surface of the flexible film and the mat surface of the flexible mat lying thereon or, if no mat is used, of the coupling surface of the treatment machine lying thereon, should therefore be eliminated on the coupling. This usually takes place by air suction. In this context, however, the fluid contacting of this space is complicated. There is in particular the problem that a self-sealing of the film takes place by an application of the film onto the mat or onto the coupling surface so that air islands remain.

It is therefore known from DE 101 57 924 C1 and DE 102 24 750 A1 to realize the air transport by means of integrated mat passages, predetermined in a defined manner, on the rear side of the machine mat at the machine side. The air line from the surface of the flexible film through the mat to the air passages arranged on the machine side takes place locally through uninterrupted slots in the region of the mat passages. The air transport however, hereby only takes place at precisely defined points of the flexible film of the cassette at which the air is sucked off through the slots in the mat to the mat passages arranged on the machine side. These mat passages therefore have to be located in the region of the liquid-conducting passages of the cassette to ensure a good suction there, which can lead to safety problems. Such a machine mat having integrated mat passages and slots is moreover cost-intensive in manufacture and complex and/or costly in cleaning. The sensor surface is thus also no longer ideally protected from environmental influences and hermetically sealed by the mat so that hygienic problems also result. There is moreover the need to further improve the reliability of the air suction since the inclusion of air islands can still occur due to the only local suction through the slots.

SUMMARY OF THE INVENTION

It is therefore the object of the present invention to achieve a cost-effective, reliable and hygienic air suction.

This object is solved in accordance with the invention by an apparatus for treating a medical liquid that includes a treatment machine having a coupling surface, with a cassette made of a hard part and having liquid-conducting passages which are covered by a flexible film being able to be coupled to the coupling surface of the treatment machine. In accordance with the invention, in this connection, in the coupled state of the cassette, a layer of an air-permeable porous material is arranged between the flexible film and the coupling surface, at least in partial regions, and air can be sucked out areally through the layer during the coupling process and/or with a coupled cassette. In accordance with the invention, air is no longer only selectively sucked out at some points through the slots in the flexible mat so that air islands may remain, as in the prior art, but is rather sucked out areally through the layer of an air-permeable porous material. A full-area suction of the air out of the region between the flexible film and the coupling surface is thereby possible, with air inclusions, which can never be precluded with only local suction, being reliably prevented. In addition, the poorly cleanable design of the flexible mat having mat passages can be dispensed with and a flexible mat can be used substantially without openings or no mat at all can be used.

It is possible in this context in accordance with the invention that air can already be sucked out particularly advantageously during the coupling process, in particular shortly before the end of the coupling process. The contact pressure is increased up to a maximum value in this connection on the coupling of the cassette. The suction can already be begun in this context as soon as the cassette contacts the coupling surface, but before the cassette is pressed on with a maximum pressing force. A vacuum can already be sucked out during this short phase. The porous material or the structuring is in particular compressed still less strongly in this phase and thus conducts air better. The suction of the air can, however, also take place with a completely coupled cassette.

The air can advantageously be sucked out through the layer of an air-permeable porous material along the plane of the layer in this connection. An air removal along the coupling plane is thereby made possible, whereas simultaneously the actuators and sensors can have an effect perpendicular to the coupling plane. It is sufficient in this connection to have fluid contact to the space between the film and the coupling surface at one or more suction points and to connect the space to a suction apparatus, with the air being sucked out areally from there along the coupling plane. If a mat is provided, the flexible mat which otherwise has no perforations can have openings at one or fewer points for fluid contacting of the air-permeable porous layer.

Due to the layer made of an air-permeable, in particular porous material, the vacuum for suction can act in the whole region of the layer made of an air-permeable porous material, which makes possible a full area, reliable suction. The material of the layer is advantageously air-permeable both along the main plane of the layer and also transversely to the main plane of the layer. The air transport can hereby in particular also take place in the material layer along its main plane, whereby the air between the surface of the flexible film and the coupling surface is reliably sucked out.

The layer of an air-permeable porous material is advantageously arranged directly on the flexible film in the coupled state of the cassette. A direction suction of the air from the surface of the flexible film thereby results so that a reliable coupling is made possible.

Further advantageously, the layer made of an air-permeable porous material comprises a nonwoven material. Such a nonwoven material permits the air transport described above, with it providing a uniform contact between the coupling surface and the film and thus between the sensors and actuators and the film, but simultaneously ensures the areal suction in the plane between the flexible film and the coupling surface or the flexible mat.

Further advantageously, the layer of an air-permeable material is arranged over the whole area of the flexible film. A cost-effective and simple possibility thus results to permit the air suction over a full surface of the layer made of an air-permeable material. It is, however, also possible for specific applications only to provide such a layer of an air-permeable material in part regions.

Further advantageously, the cassette is pressed with the coupling surface in the coupled state, with the pressure transmitted over the layer made of an air-permeable material orthogonally to its plane during the coupling process and/or with a coupled cassette pressing the film in a fluid tight fashion with the liquid-conducting passages of the hard part of the cassette, but with the layer made of an air-permeable material remaining air-permeable along its plane. The layer made of an air-permeable porous material can thus transmit the pressure required for the sealing of the liquid-conducting passages by the interaction between the webs of the hard part and the film which is pressed onto the webs. At the same time, however, it remains gas-permeable along its plane and thus provides an areal suction of the air between the film and the coupling surface.

Further advantageously, the treatment machine has a flexible mat, in particular a silicone mat, arranged on the coupling surface and the cassette can be coupled to the coupling surface of the treatment machine via the flexible mat.

In an advantageous embodiment, the treatment machine has a flexible mat arranged on the coupling surface, with the cassette being able to be coupled to the coupling surface of the treatment machine via the flexible mat and a layer of an air-permeable material being arranged between the flexible film and the flexible mat in the coupled state of the cassette. The flexible mat can hereby seal the coupling surface in a fluid tight manner and thus provide an arrangement which is particularly simple to clean and is hygienic, while the suction takes place via the air-permeable layer arranged between the flexible mat and the flexible film. Silicone or another suitable elastomer can be used as the material for the flexible mat in this context. In this connection, a porous material layer such as a nonwoven material in turn proffers itself as an air-permeable layer.

In the present invention, it is, however, also possible due to the areal suction of the air along the coupling plane to dispense with the flexible mat between the flexible film of the cassette and the coupling surface of the treatment machine and only to provide a layer of an air-permeable porous material such as a nonwoven so that the flexible film of the medical cassette lies directly on the coupling surface of the treatment machine via the layer made of an air-permeable material without a mat therebetween and the air suction takes place directly between the coupling surface and the flexible film.

The present invention further includes an apparatus for treating a medical liquid which includes a treatment machine having a coupling surface and a flexible mat arranged on the coupling surface, with a cassette made from a hard part having liquid-conducting passages, which are covered by a flexible film, being able to be coupled to the coupling surface of the treatment machine via the flexible mat, with the flexible mat comprising an air-permeable material and being configured such that air is sucked out in a region of the flexible mat without openings during the coupling process and/or with a coupled cassette, and indeed along the plane of the flexible mat and/or through the flexible mat. By the use of a permeable mat material, it is thus possible to dispense with an additional layer made of an air-permeable material since the areal suction takes place via the flexible mat itself. The supply of the vacuum can then take place via corresponding passages in the coupling surface of the treatment machine. Since thin silicone layers have a certain permeability for air, the flexible mat can be formed of silicone and can be made very thin in the regions in which air should be sucked out so that air can be sucked out directly through the mat by application of a correspondingly high vacuum. It is thus possible to dispense with slots through the mat which make cleaning more difficult. The coupling surface is moreover further sealed in a liquid tight manner.

Alternatively or additionally to the layer described above of an air-permeable porous material or to the flexible mat of an air-permeable material, however, the surface of the film or the surface of the flexible mat facing the film can have a structuring via which air can be sucked out.

The present invention therefore further includes an apparatus for treating a medical liquid which includes a treatment machine having a coupling surface, with a cassette made of a hard part having liquid-conducting passages which are covered by a flexible film being able to be coupled to the coupling surface of the treatment machine. In this connection, in accordance with the invention, the surface of the flexible film has a structuring through which air can be sucked out along the structuring of the film during the coupling process and/or with a coupled cassette. A secure suction of the air out of the region between the film and the coupling surface or mat is thus also possible along the coupling plane in that the air is sucked out through the passages formed by the structuring of the film surface. The structuring thus likewise permits an areal suction of the air and thus prevents the formation of air islands, with it being provided at least in the regions where an air-free coupling is required. The structuring in the surface of the film is advantageously small enough in this context so that no fluctuations, or only minimal fluctuations, occur in the pressing force between the flexible film and the webs of the hard part, but is large enough so that the passages arising through the structuring are not completely closed by the pressure between the coupling surface or mat and the film, but remain air-conducting.

The structuring can take place by stamping of the film surface in this connection. Alternatively, a structuring can also be introduced directly on the extrusion of the film.

It is furthermore possible to apply a structuring to the side of the flexible material facing the film. The present invention therefore further includes an apparatus for treating a medical liquid which includes a treatment machine having a coupling surface and a flexible mat, in particular a silicone mat arranged on the coupling surface, with a cassette made of a hard part having liquid-conducting passages which are covered by a flexible film being able to be coupled to the coupling surface of the treatment machine via the flexible mat. In this connection, in accordance with the invention, the surface of the flexible mat facing the flexible film has a structuring through which air can be sucked out along the structuring of the flexible mat during the coupling process and/or with a coupled cassette. The suction through the structuring of the surface of the flexible mat takes place in precisely the same way as the suction through the structuring of the flexible film such as was described above.

The structuring of the film, however, has the decisive advantage with respect to a structuring of the surface of the mat facing the film that the surface of the mat facing the film can be made smooth and is thus easy to clean. The cassette is, in contrast, anyway a disposable part so that it does not have to be cleaned after use, but is disposed of.

Advantageous embodiments of the structuring which can be used both for the structuring of the flexible film and for the structuring of the mat surface will be described hereinafter.

The structuring advantageously has a net structure and/or a meandering-like and/or a linear structure. The air can be sucked out simply and reliably areally through a net structure, in particular, advantageously a honeycomb structure. A direct suction in specific regions can, in contrast be achieved by a meandering-like structure.

Further advantageously, the structuring is made anisotropic and/or inhomogeneous. It is thus possible to realize an anisotropic suction by the selection of the suitable structure in that e.g. the passages are made larger from left to right than from top to bottom. The structure on the surface can also be made inhomogeneous. It is, for example, hereby possible to realize a uniform suction of the air in the surface, even if the space between the film and the mat is only in fluid contact with the suction apparatus at one point.

The aspect ratio of the channels which arise is important for the achievable suction power with such a structuring. The width of the passages is advantageously less than their depth in this context. The passages are not closed by such narrow, deep passages on the pressing of film and mat so that the suction remains possible. The shallower the passages, the larger the risk of sealing by a partial contact of the film on the mat would be. It the passages become too wide, the risk moreover increases that the pressing on the smooth rear side of the film with the webs of the hard part becomes too non-homogeneous and that leaks occur on this side between the liquid-conducting passages.

In a further embodiment, the structuring of the film surface or of the mat surface can extend along the liquid-conducting passages. Only a lower volume thereby has to be evacuated so that the time required for the suction or for an initial leaktightness test is reduced. In addition, the air is only sucked out where there is actually a need for an air-free connection between the film and the flexible mat. Such an air-free coupling is, in contrast, not necessary in the regions without liquid-conducting passages. The structuring can therefore advantageously extend along the liquid-conducting passages in meander-like and/or linear form.

In this context, the structuring, however, advantageously converges in one or more regions outside the liquid-conducting passages which form suction points. A simple connection, e.g. with a suction device, can thus take place in these regions outside the liquid-conducting passages, whereas the structuring extending from the suction point into the regions of the liquid-conducting passages provides a reliable suction of the air out of these regions.

The structuring advantageously extends substantially perpendicular to the passage web edge on the transition from the region with liquid-conducting passages to the region outside the liquid-conducting passages. A uniform pressing of the film with the passage web edges is hereby ensured without the structuring losing its air-conducting function due to the pressing.

The structuring advantageously has a spacing from the passage web edges in the regions in which it does not traverse the passage web edges. The structuring is thus only capable of draining in the liquid-wetted film areas required from a technical process aspect. No air suction is necessary in contrast in the other regions due to the high contact pressure between the film and the hard part.

The structuring is furthermore advantageously made such that there is no direct connection between regions of the film with different liquid-conducting passages. This has the advantage on a rupture of the film that the liquid cannot spread over the whole cassette along the structuring. Ruptures in a region without liquid-conducting passages thus in particular also remain without consequences. Even on a rupture of the film in a region of the liquid-conducting passages, the liquid is only sucked to the suction point along the structuring, whereas a leak beyond the passage web edges between the liquid-conducting passages is prevented.

However, a good and reliable pressing and air suction can also be achieved on the use of a honeycomb structure which naturally does not extend along the liquid-conducting passages and with which the structuring is not always perpendicular on the passage web edges. The simple and cost-effective manufacture is the advantage of such a design.

The cassette in the method in accordance with the invention is advantageously pressed with the coupling surface in the coupled state, with the film being pressed in a fluid-tight manner with the liquid-conducting passages of the hard part of the cassette, but with the structuring along its plane allowing air transport.

The present invention further includes an apparatus for treating a medical liquid which includes a treatment machine having a coupling surface and a flexible mat, in particular a silicone mat arranged on the coupling surface, with a cassette made of a hard part having liquid-conducting passages which are covered by a flexible film being able to be coupled to the coupling surface of the treatment machine via the flexible mat. In accordance with the invention, air can be sucked out along a plane between the flexible film and the surface of the flexible mat facing the flexible film during the coupling procedure and/or with a coupled cassette. Equipping the flexible mat with the complex and/or expensive mat passages and slots which are difficult to clean can hereby be dispensed with. The air can rather be sucked out reliably and simply between the mat surface and the flexible film. The suction advantageously takes place via a layer of an air-permeable material arranged at least in part regions or via a structuring of the flexible film or of the mat surface. The advantages already described above hereby result.

In accordance with the invention, air is thus no longer only sucked out selectively through the slots in the flexible material as in the prior art, but rather areally along the plane between the film and the mat. It is hereby sufficient to have fluid contact to the space between the film and the coupling surface at one or more points and to connect the space to a suction apparatus, with the air being sucked out areally from there along the coupling plane between the film and the mat. The cost-intensive design of the flexible mat with mat passages can thus be dispensed with. In addition, a secure air-free coupling is ensured between the film and the mat without the mat having to have slots so that a liquid-tight and thus ideally hygienically cleanable machine surface again becomes possible.

The suction of the air advantageously takes place via a structure which is arranged in the region between the flexible film and the flexible mat. An air conduction along the coupling plane is thus made possible, whereas simultaneously the actuators and sensors can have an effect perpendicular to the coupling plane. It is in particular advantageously a case of an areal structure such as the layer already named above made of an air-permeable material or a structuring of the surface of the film or of the mat. A full-area suction of the air out of this region is thereby possible, with air inclusions, which can never be precluded with only local suction, being reliably prevented.

Further advantageously, the apparatus in accordance with the invention has at least one suction device. A vacuum can be made available via this suction device, said vacuum being connected to the region between the flexible film and the flexible mat or the coupling surface and thus making the suction possible. It can be of advantage in this context to implement the suction device in a multiple fashion to improve the test capability of the suction device.

Further advantageously, with the apparatus in accordance with the invention, the air conducting layer is in fluid connection with the suction device at one or more points outside the region of the liquid-conducting passages independently of via which structure the areal suction is realized. Since the suction takes place along the coupling plane, it is no longer necessary in the present invention to make a fluid connection with a vacuum apparatus available directly in the region of the liquid-conducting passages.

Further advantageously, in the apparatus in accordance with the invention, the suction takes place via at least one valve arranged in the coupling surface of the treatment machine. Said valve is opened e.g. by pressing the cassette onto the coupling surface of the treatment machine by means of a plunger and then automatically sucks the air out of the air-conducting layer.

Alternatively, the suction can also take place through the cassette. In this connection, a suction opening with a hydrophobic membrane can be provided on the cassette. The suction therefore advantageously takes place via one or more suction openings which are arranged in the hard part of the cassette and which are advantageously provided with a hydrophobic membrane. A simple fluid contacting of the air-conducting layer is hereby possible.

Further advantageously, the apparatus in accordance with the invention has an optical sensor for the recognition of leaks, in particular by scattered light wetting detection. A simplified contactless leak detection hereby results, in particular in conjunction with a structuring of the film surface which varies its reflection properties by discharge of liquid, which can be detected by the optical sensor.

Further advantageously, the apparatus in accordance with the invention has a control which carries out an automatic suction of the air. In this context, the control controls the suction device and thus automatically provides an air-free coupling of the medical cassette.

Further advantageously, the control carries out an automatic check of the leaktightness of the medical cassette. This can be carried out, as will be described further below, by a check of the vacuum on the air suction.

Further advantageously, a medical cassette, which will be shown in the following, is used in the apparatus in accordance with the invention such as have already been described.

The medical cassette of the present invention in this context includes a hard part having liquid-conducting passages which are covered by a flexible film, with the cassette being able to be coupled to a coupling surface of a treatment machine. In this connection, in accordance with the invention, a structure is arranged on the flexible film through which air can be sucked out along the plane of the film surface during the coupling process and/or with a coupled cassette. As already shown in detail with respect to the apparatus for treating a medical liquid, it is hereby possible to ensure a secure and reliable suction of the air between the flexible film and the mat or the coupling surface of the treatment machine. It is of particular advantage in this context for the structure to form a component of the medical cassette since this is a disposable part and therefore does not have to be cleaned after use. The structure for the air suction thus also does not have to satisfy any special conditions with respect to cleanability.

A layer of air-permeable material, in particular porous material, through which air can be sucked out areally along the plane of the material layer in the coupled state of the cassette is advantageously arranged on the flexible film at least in part regions. The advantages of such an arrangement have already been shown above with respect to the apparatus. The layer of an air-permeable material, in particular a porous material, which is arranged on the flexible film allows a reliable and uniform areal suction of the air.

The layer of an air-permeable material is advantageously arranged over the whole area of the flexible film. An inexpensive and simple arrangement can thus be realized in which air can be sucked out over the whole area between the flexible film and the coupling surface of the treatment machine.

The layer of an air-permeable material is advantageously welded to the cassette in a peripheral marginal region. The layer of an air-permeable material thereby forms a unit with the cassette and is securely held thereon. Further advantageously, the welding of the layer of an air-permeable material takes place in a single workstep together with the welding of the film with the hard part. A cost-effective production can thus be realized.

Further advantageously, the weld forms a gas-tight barrier along the plane of the material layer. It is hereby ensured by the welding that air is only sucked out along the plane of the material layer in the region in which the cassette is pressed with the treatment machine. Otherwise air could be sucked out of side regions and thus prevent a venting of the region between the flexible film and the treatment machine. The fact can be utilized in this context that on the welding of the layer of an air-permeable material onto the film, the structure of the advantageously porous material layer is modified such that a gas-tight barrier is created. Sealing is therefore effected with the flexible mat or the coupling surface at this point against a material layer made air-impermeable. The layer of an air-permeable material is advantageously welded to the hard part of the cassette. For this purpose, the layer of an air-permeable material advantageously comprises a material which can be welded to the plastic from which the hard part of the cassette is produced.

Alternatively or additionally, the hard part of the cassette can have a peripheral marginal region into which the structure, in particular the layer of an air-permeable material, does not extend so that this marginal region forms a sealing web on pressing. This sealing web formed by the marginal region without structure therefore ensures that the space between the film and the mat or the coupling surface of the treatment machine can be reliably vented. For this purpose, the layer of an air-permeable material or a structuring can in particular be dispensed with in the marginal region of the cassette.

Further advantageously, the flexible film is welded to the hard part of the cassette in the peripheral marginal region. This peripheral marginal region can thus be used for the welding to the flexible film as in the prior art and can moreover serve as a sealing web for the structure.

Further advantageously, in the present invention the layer of an air-permeable material is connected, in particular adhesively bonded and/or spot welded and/or pasted and/or laminated and/or tacked to the film. A reliable grip of the layer of an air-permeable material on the flexible material is hereby ensured, e.g. even if the layer is not welded to the hard part in the marginal region.

Further advantageously, with the medical cassette of the present invention, the pressure transmitted during the coupling process and/or with a coupled cassette via the structure, in particular via the layer of an air-permeable material, orthogonally to its plane presses the film with the liquid-conducting passages of the hard part of the cassette in a fluid-tight manner. The structure, in particular the layer of an air-permeable material, in contrast remains gas-permeable along its plane. A reliable pressing of the film and the hard part is thus possible in which no leaks occur between the liquid-conducting passages, with nevertheless, however, a reliable air suction via the areal structure remaining possible. This is achieved by a corresponding configuration of the material layer, e.g. of a nonwoven, or by the corresponding configuration of the structuring of the surface of the flexible film.

Further advantageously, the layer made of an air-permeable material comprises a non-woven. Such a nonwoven is ideally suited for the uniform transmission of pressure and for the suction along its plane.

In a further embodiment, the surface of the flexible film of the medical cassette of the present invention can advantageously have a structuring through which air can be sucked out along the plane of the film in the coupled state of the cassette. It can hereby be achieved in a simple manner that the air can be reliably removed from the region between the film and the mat or between the film and the coupling surface of the treatment machine without air inclusions or air islands being formed. The arrangement of the structuring on the surface of the film is of particular advantage in this connection since the cassette is anyway disposed of after use and thus does not have to be cleaned.

As already shown with respect to the apparatus for treating a medical liquid, the structuring advantageously has a net structure and/or a meander-like structure and/or a linear structure. Further advantageously, the structuring is made anisotropic and/or inhomogeneous. It is equally further of advantage for the width of the passages formed by the structuring to be less than the depth of these passages since they thereby do not close on the pressing with the treatment machine and nevertheless permit a uniform pressing of the smooth rear of the film with the webs of the hard part.

In a further advantageous embodiment, the structuring extends along the liquid-conducting passages, with use in particular being made of a meander-like and/or a linear structure. The volume which has to be evacuated can hereby be reduced.

Further advantageously, the structuring converges in one or more regions outside the liquid-conducting passages which form suction points. A simple suction can hereby take place in this region, whereas an air-free coupling is ensured in this region along the liquid-conducting passages via the structuring.

The structuring advantageously extends substantially perpendicular to the passage web edge on the transition from the region with liquid-conducting passages to the region outside the liquid-conducting passages. A uniform pressing of the film with the passage web edge is hereby ensured with a simultaneously good air suction.

The structuring advantageously has a spacing from the passage web edges in the regions in which it does not traverse the passage web edges. It can hereby be prevented that the liquid spreads over the whole cassette along the structuring in the event of a rupture. A better pressing of the film with the passage web edges is moreover achieved.

The structuring is furthermore advantageously made such that there is no direct connection between regions of the film with different liquid-conducting passages. This has the advantage on a rupture of the film that the liquid cannot spread over the whole cassette along the structuring. Ruptures in a region without liquid-conducting passages thus in particular also remain without consequences. Even on a rupture of the film in a region of the liquid-conducting passages the liquid is only sucked to the suction point along the structuring, whereas a leak beyond the passage web edges between the liquid-conducting passages is prevented.

Further advantageously, the hard part of the medical cassette in accordance with the invention has containment webs which connect the passage rim sealing webs and form closed areas in a press-tight manner. The suction point is advantageously disposed in such an area closed in a press-tight manner such that on a film rupture the leak liquid only reaches this area and no direct contact is possible between the individual liquid-conducting regions.

Further advantageously, the medical cassette in accordance with the invention has at least one suction opening arranged at the hard part of the cassette. The space between the film and the mat or the coupling surface can have a fluid contact for suction via this suction opening. The flexible mat can hereby be made throughgoing and thus ideally cleanable on the machine side.

The suction opening is advantageously arranged outside the region of the liquid-conducting passages in this context. Security is hereby increased since a failure of the weld only results in a contamination of the suction device or of the hydrophobic membrane arranged in the suction passage on a simultaneous rupture of the film at a passage point or on a simultaneous failure of a sealing web.

The flexible film is advantageously welded to the hard part of the cassette around the suction opening.

In this context, the annular weld seam around the suction opening advantageously has a structuring so as not to impair the air suction by the weld seam. This is in particular important with a structuring of the film surface and can e.g. be achieved via a corresponding structure of the welding stamp.

Alternatively or additionally, the region of the weld seam can also be lowered with respect to the pressing plane of the cassette. An impairment of the air suction by the weld seam can also be prevented by this. This is in particular also of particular advantage on the use of a layer of air-permeable material.

Further advantageously, a hydrophobic filter is arranged at the suction opening. In this context, the suction opening or the suction openings are advantageously closed by one or more hydrophobic filters in a liquid-tight manner. Hydrophobic filters are liquid-tight and simultaneously gas-permeable.

The present invention further includes methods for coupling a cassette to a treatment machine which permit a reliable air-free coupling.

The present invention in this context includes a method for coupling a cassette made of a hard part having liquid-conducting passages which are covered by a flexible film to the coupling surface of a treatment machine for treating a medical fluid comprising the steps: coupling of the Medical cassette to the coupling surface of the treatment machine and suction of air between the flexible film and the coupling surface of the treatment machine during the coupling process and/or with a coupled cassette, with the suction taking place areally via a layer of an air-permeable porous material arranged at least in part regions between the flexible film and the coupling layer. The steps of coupling and of suction can be carried out either sequentially in this process or at least partly simultaneously in that the suction is started while the coupling process is still ongoing.

Alternatively, the suction can also take place along a structuring of the surface of the flexible film and/or along a structuring of a surface of a flexible mat facing the flexible film via which the cassette is coupled to the coupling surface. The advantages already shown with respect to the apparatus, in particular a reliable suction of the air from the region between the flexible film and the coupling surface of the treatment machine, hereby result.

The invention furthermore includes a method for coupling a cassette made of a hard part having liquid-conducting passages which are covered by a flexible film to the coupling surface of a treatment machine for treating a medical fluid comprising the steps: coupling of the medical cassette to the coupling surface of the treatment machine via a flexible mat arranged on the coupling surface, suction of air between the flexible film and the flexible mat during the coupling process and/or with a coupled cassette, with the suction taking place in regions of the flexible mat without interruptions, and indeed along the plane of the flexible mat and/or through the flexible mat, for which purpose the mat comprises an air-permeable material.

The present invention furthermore includes a method for coupling a cassette made of a hard part having liquid-conducting passages which are covered by a flexible film to the coupling surface of a treatment machine for treating a medical fluid comprising the steps: coupling of the medical cassette to the coupling surface of the treatment machine via a flexible mat, in particular a silicone mat, arranged on the coupling surface and suction of air between the flexible film and the flexible mat during the coupling process and/or with a coupled cassette, with the suction taking place along the plane between the flexible film and the surface of the flexible mat facing the flexible film. The advantages already described above also hereby result. The flexible material can in particular be made inexpensively and easy to clean in this context.

In this context, in the method in accordance with the invention, a medical cassette and/or an apparatus for treating a medical liquid such as was/were already shown above is/are advantageously used.

The present invention further relates to a method for checking the leaktightness of a medical cassette made of a hard part having liquid-conducting passages which are covered by a flexible film, in particular before the filling of the medical cassette, comprising the steps: coupling a medical cassette to a coupling surface of a treatment machine, suction of air between the flexible film and the coupling surface of the treatment machine during the coupling process and/or with a coupled cassette, in particular area suction, checking the leaktightness of the medical cassette using the vacuum which arises, with the check of the leaktightness taking place during and/or after the coupling of the cassette. Since no vacuum can be built up in the case of a film leak on the suction of the air, it is possible in accordance with the invention to determine and to display too high a leak rate via the vacuum monitoring and vacuum evaluation of the air suction. A leak in the disposable film can thus above all be recognized initially before the filling of the disposable and before starting treatment. The defective disposable can thereby be replaced by an intact one. There is thus the possibility due to the continuous evacuation of determining leaks in the film and of replacing defective disposables.

This is in particular facilitated by the areal suction of the present invention. In contrast, self-seatings would occur between the film and the mat without the areal suction, which would make a check more difficult. With such a process, a medical cassette and/or an apparatus for treating a medical liquid such as have been described above can advantageously be used.

The applicant reserves the right to file divisional applications to any aspect of the present invention described in this application, and in particular also to those aspects which are not the subject matter of the claims of the present application. In particular, the present invention comprises the following aspects, which are subject matter of the present application also on their own and independently of the preceding description:

1. An apparatus for treating a medical liquid which includes a treatment machine having a coupling surface, with a cassette made of a hard part having liquid-conducting passages which are covered by a flexible film being able to be coupled to the coupling surface of the treatment machine, characterized in that, in the coupled state of the cassette, a layer of an air-permeable porous material is arranged between the flexible film and the coupling surface, at least in partial regions, and air can be sucked out areally through said layer during the coupling process and/or with a coupled cassette.

2. An apparatus in accordance with aspect 1, wherein the air can be sucked out through the layer of an air-permeable porous material along the plane of the layer.

3. An apparatus in accordance with either of aspects 1 or 2, wherein the layer of an air-permeable porous material is arranged directly on the flexible film in the coupled state of the cassette.

4. An apparatus in accordance with one of the aspects 1 to 3, wherein the layer of an air-permeable porous material includes a nonwoven.

5. An apparatus in accordance with one of the aspects 1 to 4, wherein the layer of an air-permeable porous material is arranged over the whole area on the flexible film.

6. An apparatus in accordance with one of the aspects 1 to 5, wherein the cassette is pressed with the coupling surface in the coupled state, with the pressure transmitted over the layer made of an air-permeable material orthogonally to its plane during the coupling process and/or with a coupled cassette pressing the film in a fluid tight fashion with the liquid-conducting passages of the hard part of the cassette, but with the layer made of an air-permeable material remaining air-permeable along its plane.

7. An apparatus in accordance with any one of the aspects 1 to 6, wherein the treatment machine has a flexible mat arranged on the coupling surface, with the cassette being able to be coupled to the coupling surface of the treatment machine via the flexible mat and a layer of an air-permeable material being arranged between the flexible film and the flexible mat in the coupled state of the cassette.

8. An apparatus for treating a medical liquid which includes a treatment machine having a coupling surface and a flexible mat arranged on the coupling surface, with a cassette made of a hard part having liquid-conducting passages which are covered by a flexible film being able to be coupled to the coupling surface of the treatment machine via the flexible mat, characterized in that the flexible mat comprises an air-permeable material and is configured such that air is sucked out in a region of the flexible mat without interruptions during the coupling process and/or with a coupled cassette, and indeed along the plane of the flexible mat and/or through the flexible mat.

9. An apparatus for treating a medical liquid which includes a treatment machine having a coupling surface, with a cassette made of a hard part having liquid-conducting passages which are covered by a flexible film being able to be coupled to the coupling surface of the treatment machine, characterized in that the surface of the flexible film has a structuring through which air can be sucked out along the structuring of the film during the coupling process and/or with a coupled cassette.

10. An apparatus for treating a medical liquid which includes a treatment machine having a coupling surface and a flexible mat arranged on the coupling surface, with a cassette made of a hard part having liquid-conducting passages which are covered by a flexible film being able to be coupled to the coupling surface of the treatment machine via the flexible mat, characterized in that the surface of the flexible mat facing the flexible film has a structuring through which air can be sucked out along the structuring of the flexible mat during the coupling process and/or with a coupled cassette.

11. An apparatus in accordance with either of aspects 9 or 10, wherein the structuring has a net structure and/or a meander-like and/or linear structure.

12. An apparatus in accordance with either of aspects 9 or 10, wherein the structuring is made anisotropoic and/or inhomogeneous.

13. An apparatus in accordance with either of aspects 9 or 10, wherein the structuring extends along the liquid-conducting passages.

14. An apparatus in accordance with aspect 13, wherein the structuring converges in one or more regions outside the liquid-conducting passages which form suction points.

15. An apparatus in accordance with one of the aspects 9 to 14, wherein the structuring extends substantially perpendicular to the passage web edge on the transition from the region with liquid-conducting passages to the region outside the liquid-conducting passages.

16. An apparatus in accordance with one of the aspects 13 to 15, wherein the structuring has a spacing from the passage web edges in the regions in which it does not traverse the passage web edges.

17. An apparatus in accordance with one of the aspects 13 to 16, wherein the structuring is made such that there is no direct connection between regions of the film with different liquid-conducting passages.

18. An apparatus in accordance with one of the aspects 9 to 17, wherein the cassette is pressed with the coupling surface in the coupled state, with the film being pressed in a fluid-tight manner with the liquid-conducting passages of the hard part of the cassette, but with the structuring along its plane allowing air transport.

19. An apparatus for treating. a medical liquid which includes a treatment machine having a coupling surface and a flexible mat, in particular a silicone mat, arranged on the coupling surface, with a cassette made of a hard part having liquid-conducting passages which are covered by a flexible film being able to be coupled to the coupling surface of the treatment machine via the flexible mat,
characterized in that
air can be sucked out along a plane between the flexible film and the surface of the flexible mat facing the flexible film during the coupling procedure and/or with a coupled cassette.

20. An apparatus in accordance with one of the preceding aspects comprising at least one suction device.

21. An apparatus in accordance with aspect 20, wherein the air-conducting layer is in communication with a vacuum device at one or more points outside the region of the liquid-conducting passages.

22. An apparatus in accordance with one of the preceding aspects, wherein the suction takes place via at least one valve arranged in the coupling surface of the treatment machine.

23. An apparatus in accordance with one of the preceding aspects, wherein the suction takes place via one ore more suction openings arranged in the hard part of the cassette.

24. An apparatus in accordance with one of the preceding aspects, comprising an optical sensor for the recognition of leaks, in particular by scattered light wetting detection.

25. An apparatus in accordance with one of the preceding aspects, comprising a control which carries out an automatic suction of the air.

26. An apparatus in accordance with aspect 25, wherein the control carries out An automatic check of the leaktightness of the medical cassette.

27. An apparatus in accordance with one of the preceding aspects, comprising a medical cassette in accordance with one of the following aspects.

28. A medical cassette made of a hard part having liquid-conducting passages which are covered by a flexible film, with the cassette being able to be coupled to the coupling surface of the treatment machine,
characterized in that
a structure is arranged on the flexible film through which air can be sucked out along the plane of the film surface during the coupling process and/or with a coupled cassette.

29. A medical cassette in accordance with aspect 28, wherein a layer of an air-permeable material, in particular porous material, through which air can be sucked out areally along the plane of the material layer in the coupled state of the cassette is arranged on the flexible film at least in part regions.

30. A medical cassette in accordance with aspect 29, wherein the layer of an air-permeable porous material is arranged over the whole area on the flexible film.

31. A medical cassette in accordance with either of aspects 29 or 30, wherein the layer of an air-permeable material is welded to the cassette in a peripheral marginal region.

32. A medical cassette in accordance with aspect 31, wherein the weld forms a gas-tight barrier along the plane of the layer of an air-permeable material.

33. A medical cassette in accordance with one of the aspects 28 to 32, wherein the layer of an air-permeable material is welded to the hard part of the cassette.

34. A medical cassette in accordance with either of aspects 28 or 29, wherein the hard part of the cassette has a peripheral marginal region into which the structure, in particular the layer of an air-permeable material, does not extend so that this marginal region forms a sealing web on pressing.

35. A medical cassette in accordance with aspect 34, wherein the flexible film is welded to the hard part of the cassette in the peripheral marginal region.

36. A medical cassette in accordance with aspect 29, wherein the layer of an air-permeable material is connected, in particular adhesively bonded and/or spot welded and/or pasted and/or laminated and/or tacked to the film.

37. A medical cassette in accordance with either of aspects 28 or 29, wherein the pressure transmitted during the coupling process and/or with a coupled cassette via the structure, in particular via the layer of an air-permeable material, orthogonally to its plane presses the film with the liquid-conducting passages of the hard part of the cassette in a fluid-tight manner, but the structure, in particular the layer of an air-permeable material remains gas-permeable along its plane.

38. A medical cassette in accordance with aspect 29, wherein the layer of an air-permeable porous material includes a nonwoven.

39. A medical cassette in accordance with aspect 28, wherein the surface of the flexible film has a structuring through which air can be sucked out along the plane of the film in the coupled state of the cassette.

40. A medical cassette in accordance with aspect 39, wherein the structuring has a net structure and/or a meander-like structure and/or a linear structure.

41. A medical cassette in accordance with either of aspects 39 or 40, wherein the structuring is made anisotropic and/or inhomogeneous.

42. A medical cassette in accordance with either of aspects 39 or 40, wherein the structuring extends along the liquid-conducting passages.

43. A medical cassette in accordance with aspect 42, wherein the structuring converges in one or more regions outside the liquid-conducting passages which form suction points.

44. A medical cassette in accordance with one of the aspects 28 to 43, wherein the structuring extends substantially perpendicular to the passage web edge on the transition from the region with liquid-conducting passages to the region outside the liquid-conducting passages.

45. A medical cassette in accordance with one of the aspects 42 to 44, wherein the structuring has a spacing from the passage web edges in the regions in which it does not traverse the passage web edges.

46. A medical cassette in accordance with one of the aspects 42 to 45, wherein the structuring is made such that there is no direct connection between regions of the film with different liquid-conducting passages.

47. A medical cassette in accordance with one of the preceding aspects, wherein the hard part has containment webs which connect the passage rim sealing webs and form areas sealing pressed closed.

48. A medical cassette in accordance with one of the preceding aspects, comprising at least one suction opening arranged in the hard part of the cassette.

49. A medical cassette in accordance with aspect 48, wherein the suction opening is arranged outside the region of the liquid-conducting passages.

50. A medical cassette in accordance with aspect 48, wherein the flexible film is welded to the hard part of the cassette around the suction opening.

51. A medical cassette in accordance with aspect 50, wherein the annular weld seam has a structuring around the suction opening.

52. A medical cassette in accordance with aspect 50, wherein the region of the weld seam is lowered with respect to the pressing plane of the cassette.

53. A medical cassette in accordance with aspect 48, wherein a hydrophobic filter is arranged at the suction opening.

54. A method for coupling a cassette made of a hard part having liquid-conducting passages which are covered by a flexible film to the coupling surface of a treatment machine for treating a medical fluid comprising the steps:
coupling the medical cassette to the coupling surface of the treatment machine;
suction of air between the flexible film and the coupling surface of the treatment machine during the coupling process and/or with a coupled cassette,
characterized in that
the suction takes place areally via a layer of an air-permeable porous material arranged at least in part regions between the flexible film and the coupling surface.

55. A method for coupling a cassette made of a hard part having liquid-conducting passages which are covered by a flexible film to the coupling surface of a treatment machine for treating a medical fluid comprising the steps:
coupling the medical cassette to the coupling surface of the treatment machine via a flexible mat arranged on the coupling surface;
suction of air between the flexible film and the flexible mat during the coupling process and/or with a coupled cassette,
characterized in that
the suction takes place in regions of the flexible mat without interruptions, and indeed along the plane of the flexible mat and/or through the flexible mat, for which purpose the mat comprises an air-permeable material.

56. A method for coupling a cassette made of a hard part having liquid-conducting passages which are covered by a flexible film to the coupling surface of a treatment machine for treating a medical fluid comprising the steps:
coupling the medical cassette to the coupling surface of the treatment machine;
suction of air between the flexible film and the coupling surface of the treatment machine during the coupling process and/or with a coupled cassette,
characterized in that
the suction takes place along a structuring of the surface of the flexible film and/or along a structuring of a surface of a flexible mat facing the flexible film via which the cassette is coupled to the coupling surface.

57. A method for coupling a cassette made of a hard part having liquid-conducting passages which are covered by a flexible film to the coupling surface of a treatment machine for treating a medical fluid comprising the steps:
coupling the medical cassette to the coupling surface of the treatment machine via a flexible mat arranged on the coupling surface;
suction of air between the flexible film and the flexible mat during the coupling process and/or with a coupled cassette,
characterized in that the suction takes place along the plane between the flexible film and the surface of the flexible mat facing the flexible film.

58. A method in accordance with any one of the aspects 54 to 57, comprising a medical cassette and/or an apparatus for treating a medical liquid in accordance with one of the aspects.

59. A method for checking the leaktightness of a medical cassette made of a hard part having liquid-conducting passages which are covered by a flexible film, in particular before the filling of the medical cassette, comprising the steps:
coupling the medical cassette to a coupling surface of a treatment machine;
suction of air between the flexible film and the coupling surface of the treatment machine, in particular areal suction during the coupling process and/or with a coupled cassette;
checking the leaktightness of the medical cassette with reference to the created vacuum,
wherein the check of the leaktightness takes place during and/or after the coupling of the cassette.

60. A method in accordance with aspect 59, comprising a medical cassette and/or an apparatus for treating a medical liquid in accordance with one of the preceding aspects.

BRIEF DESCRIPTION OF THE DRAWINGS

The present invention will now be shown in more detail with reference to embodiments and to drawings. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
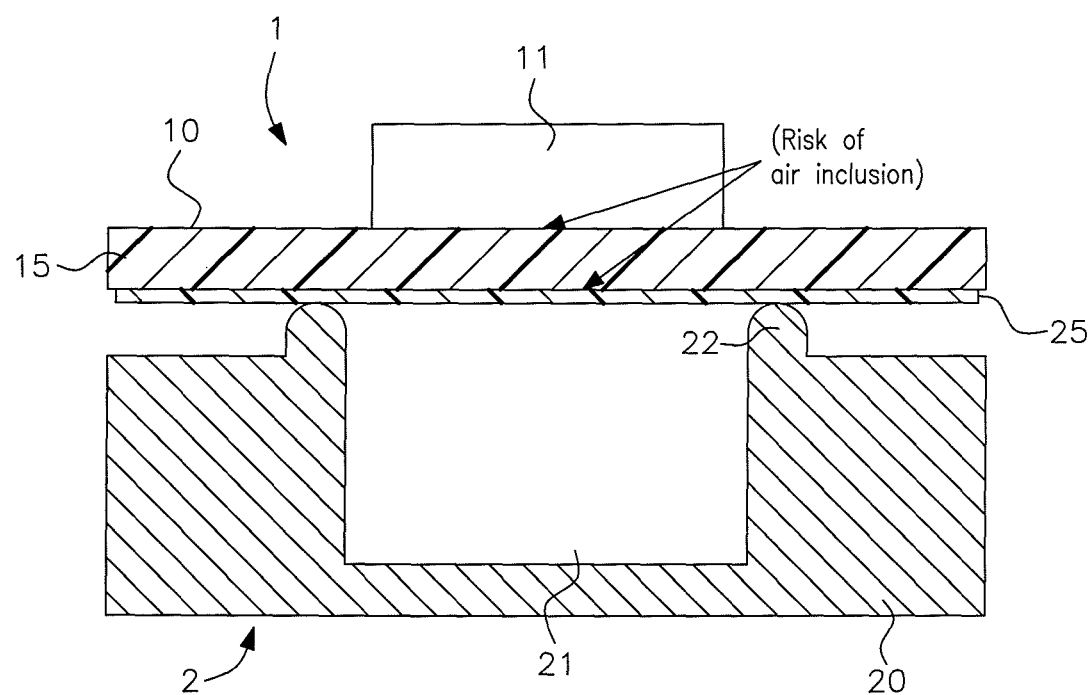
FIG. 1: an apparatus for treating a medical liquid in accordance with the prior art.

FIG. 1 shows an apparatus for treating a medical liquid such as is used in the prior art, e.g. for hemodialysis or peritoneal dialysis. Such apparatus can, however, also be used in a plurality of other fields of application in which a disposable cassette, which is also called a disposable, is used and is coupled to sensors and actuators of a treatment machine via a coupling surface.

The treatment machine 1 has a coupling surface 10 on which a sensor 11 is arranged by way of example. The cassette 2 includes a hard part 20 having a liquid-conducting passage 21 which is covered by a flexible film 25, with the liquid-conducting passage being separated in fluid-tight manner inside the cassette via laterally arranged sealing webs 22 which are pressed with the flexible film 25. In this connection, the sensor 11 is disposed opposite the liquid-conducting passage 21 which thus forms a measuring chamber, in the case of a pressure sensor a pressure measuring chamber.

Furthermore, a flexible silicone mat 15 is arranged between the film 25 and the coupling surface 10 of the treatment machine 1 on the machine side to protect the sensor surfaces of the sensor 11 from environmental influences. In addition, the machine surface is hereby hermetically sealed and thus ideally hygienically cleanable. Alternatively, however, the silicone mat 15 can also be dispensed with so that the film 25 directly contacts the coupling surface 10 of the treatment machine 1.

The difficulty exists with the coupling of sensors to the film disposable 2, however, of coupling the film 25 to the sensor surface of the sensor 11 such that correct measured values are obtained. In particular air which is enclosed in the transmission path between the disposable film 25 and the sensor surface on the insertion of the cassette produces a falsification of the measured results. This applies to pressure sensors, but also e.g. in level detection and likewise to actuators such as valves which control the liquid flows inside the cassette via a pressing of the flexible film 25 into the liquid-conducting passages 21 of the hard part 20.

Figure 2:
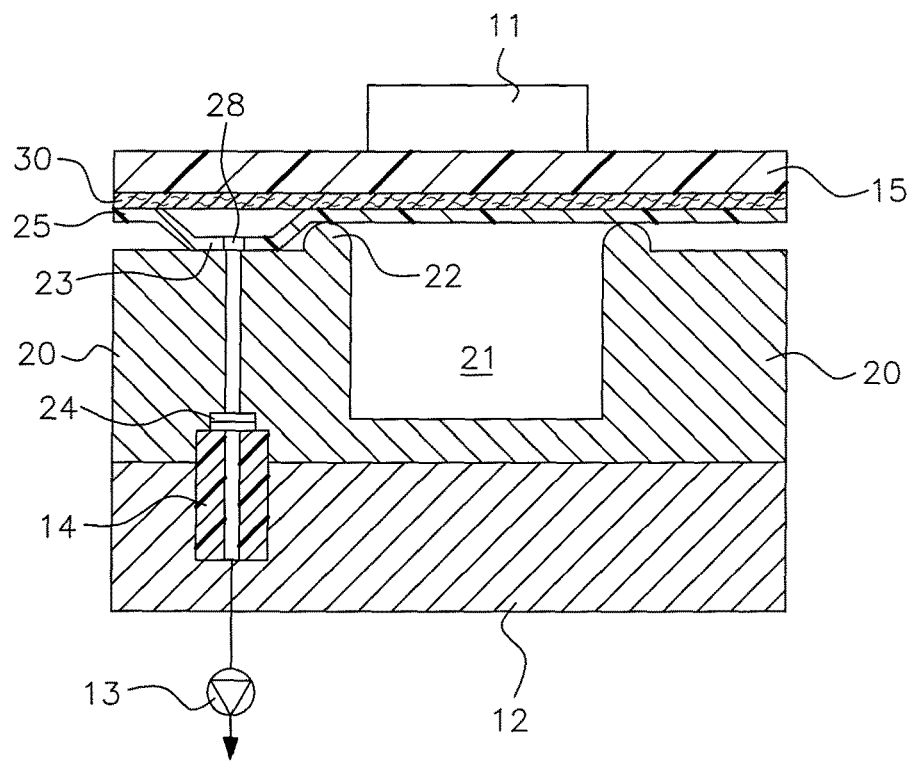
FIG. 2: an apparatus for treating a medical liquid in accordance with a first embodiment of the present invention.

A first embodiment of the present invention is now shown in FIG. 2. In this context, an areal structure between the film 25 and the mat 15 permits an areal air suction along the coupling plane. It can hereby be ensured that the space between the film 25 and the mat 15 is reliably vented without air islands remaining enclosed and falsifying the measured results due to a self-sealing by applying the film 25 to the mat 15.

In the embodiment shown in FIG. 2, the areal suction is achieved in that a layer 30 of an air-permeable, in particular porous, material, in this case a nonwoven layer, is inserted between the film 25 and the mat 15. Such a nonwoven layer is porous due to its structure, that is air can flow in the surface in this layer even if the total composite of film 25, nonwoven 30 and mat 15 is strongly pressed e.g. by the sealing webs 22.

A connection is thus obtained between the film 25 and the hard part 20 which is pressed in a fluid-tight manner, with the layer 30 of an air-permeable material, in particular porous material, nevertheless remaining permeable for air. It is thus sufficient to contact the space between the film 25 and the mat 15 at a single point with a vacuum system 13 in a fluid manner via a suction opening 28 to vent the total space between the film 25 and the mat 15 reliably and areally. A plurality of sensors 11 or actuators can hereby be coupled reliably and air-free to the film 25. The connection of the nonwoven space with the vacuum system can in this manner also be used directly after the pressing for a film leaktightness test such as would not be possible without such an air conducting layer.

The suction opening 28 is integrated in the hard part 20 of the cassette in the first embodiment and has a hydrophobic membrane 24 in the suction passage which is likewise integrated into the hard part. A contamination of the machine can hereby be prevented in the defect case of a film rupture. The suction opening 28 in the hard part 20 of the cassette is connected via a sealing element 14 to suction channels which are integrated in the machine door 12 and are in turn in communication with a vacuum system 13 on the insertion of the cassette into the treatment machine. The films has a peripheral weld with the hard part around the suction opening 28. In this context, the region of the peripheral weld is lowered with respect to the pressing level of the cassette so that the weld of the nonwoven 30 with the hard part does not represent a barrier for the air suction.

The fluid contacting of the nonwoven space takes pace outside the liquid-conducting areas of the passage structure 21. A failure of the weld between the film and the hard part around the suction opening thus only results in a contamination of the hydrophobic membrane 24 on a simultaneous film rupture on a passage point or a simultaneous failure of a sealing web 22.

Figure 3:
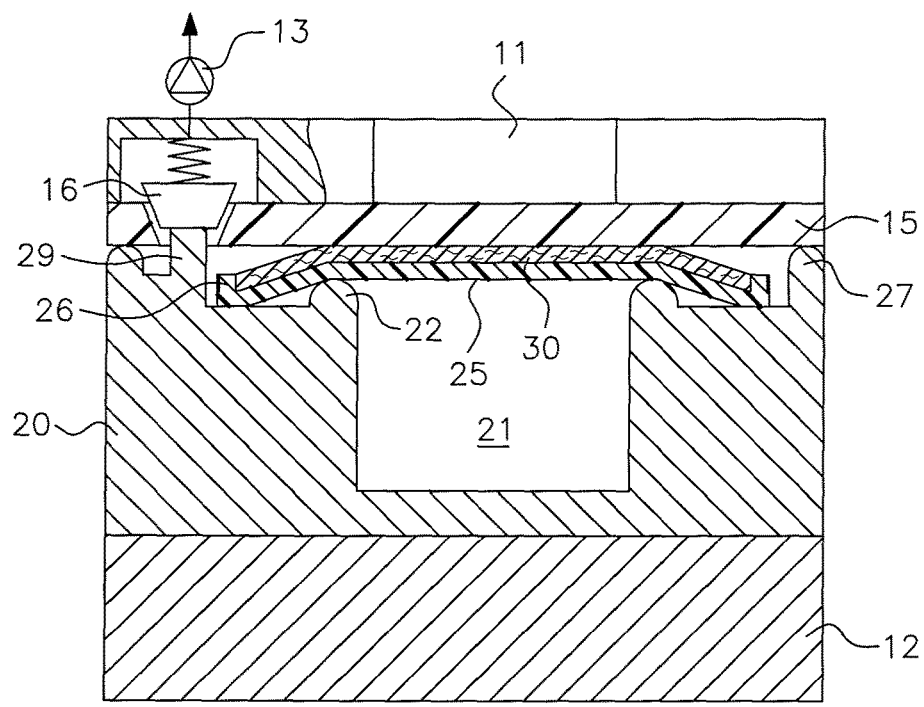
FIG. 3: an apparatus for treating a medical liquid in accordance with a second embodiment of the present invention.

A second embodiment of the present invention is shown in FIG. 3 in which the fluid contacting does not take place starting from the hard part 20, but rather from the mat side. In this connection, an opening is provided in the mat 15 and is in fluid communication with the vacuum system 13 via a valve 16. The contacting of the air-conducting layer 30 also takes place outside the region of the liquid-conducting areas of the passage structure 21 here. The hard part 20 has a plunger 29 which opens the valve 16 on the insertion of the cassette into the treatment machine. The cassette has a peripheral sealing web 27 at which no nonwoven layer 30 is provided so that an outwardly closed space arises between the film 25 and the mat 15 from which the air can be sucked out without leak air flowing in from the outside.

Alternatively to the arrangement shown in FIG. 3, an excessive intrusion of leak air into the system can also take place by other designs of a peripheral sealing rim. The fact can e.g. be utilized in this context that the nonwoven structure is modified on the welding of the nonwoven 30 to the film 25 such that a gas-tight barrier is created. A nonwoven 30 made air-impermeable can therefore be pressed with the silicone mat 15 at this point in an airtight manner. This welding ideally takes place in a single workstep together with the welding of the film with the hard part 20. For this purpose, it is advantageous to produce the nonwoven 30 from a material, e.g. from PP, which can welded with the hard part 20.

A further possibility comprises cutting out the nonwoven to be smaller than the film so that a seal can be provided peripherally directly between the film and the silicone mat. The fastening of the nonwoven 30 to the film can take place in this case e.g. by adhesive bonding and/or spot welding and/or pasting and/or laminating and/or tacking. It is moreover possible to connect the film and the nonwoven in a first workstep and then to establish the connection to the hard part in a second step.

Alternatively to the use of the nonwoven shown in the first and second embodiments, the air transport in the desired plane can be achieved in that the surface of the film 25 is structured such that an air-conducting layer arises in the film itself. This can take place, for example, by stamping a structure into the film.

Figure 4:
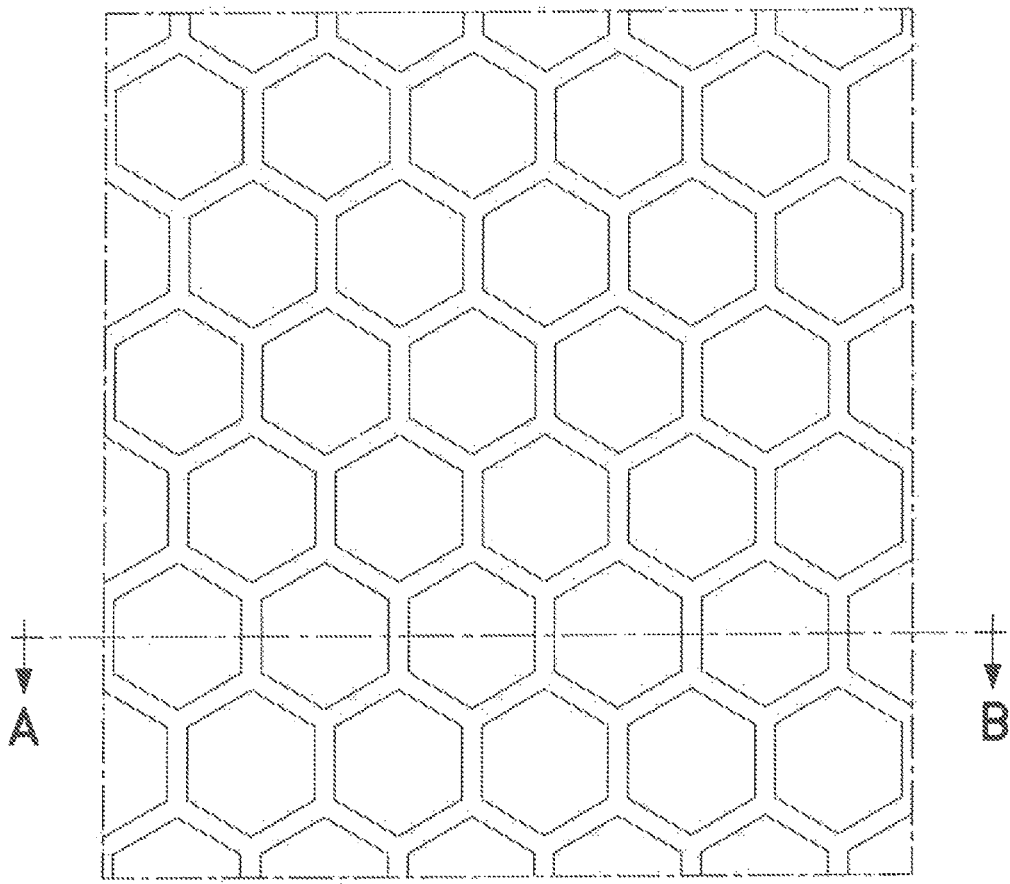
FIG. 4: a plan view as well as a sectional view of a structuring in accordance with a third embodiment of the present invention.
Figure 4:
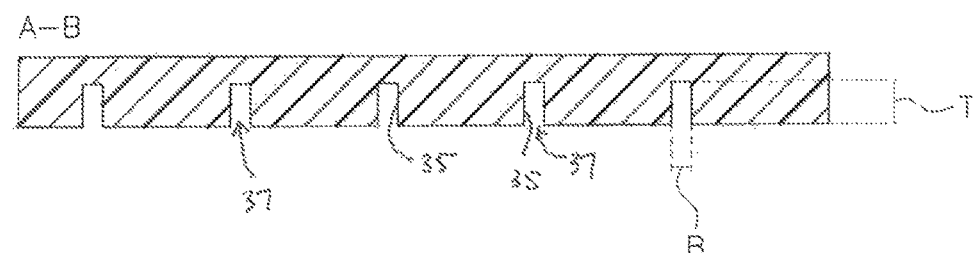

In this context, in a third embodiment, a grid-like structure can be pressed into the film so that a network of grooves 35 forming passages, generally designated by reference numeral 37, arises in the film which are separated from one another by regions of thicker material. Different geometries are conceivable, with FIG. 4 showing a honeycomb structure by way of example. It is also possible to realize an anisotropic suction by the selection of the suitable structure in that e.g. the grooves 35 forming the passages 37 are made larger from left to right than from top to bottom. The structure on the surface can also be inhomogeneous in design. The structure can likewise be of meander shape.

In this context, the geometry of the passages being created is important for the achievable suction power. Narrow, deep grooves form passages that are not closed by the silicone mat on pressing so that a suction through the passages remains possible. The shallower the grooves and resulting passages are, the higher the risk of sealing by a partial application of the film to the mat in the passages. If the passages become too wide, risk increases that the pressing on the smooth side of the film (toward the blood side and the hard part) becomes too inhomogeneous and that leaks arise on this side. Further production processes for the manufacture of the structuring of the surface of the film are available in addition to stamping. A structure can e.g. also be introduced into the film surface directly in the extrusion of the film.

Alternatively, such a structuring could also be arranged in the surface of the mat 15 facing the film 30. A reliable air suction could also hereby be made possible. However, it is a disadvantage of such an arrangement that the surface of the mat is then no longer smooth and so a cleaning of the mat surface is made difficult.

It is alternatively likewise possible to dispense with the silicone mat 15 on the use of a nonwoven 30 or of a structuring of the film surface so that the nonwoven 30 is arranged directly between the film 25 and the coupling surface 10 of the treatment machine or the structured surface of the film 25 directly contacts the coupling surface 10 of the treatment machine.

On the full area structuring of the cassette film or by generating a full area drainage layer between the film plane and the coupling plane, the total film area of the cassette up to the peripheral film weld seam A or up to the outer peripheral sealing web 8 (produced at the cassette side or at the machine side) is made passable for gases and liquids beyond all the regular passage rim sealing webs C. On the initial integrity test, it is therefore necessary to evacuate the whole area and the leaktightness of the peripheral sealing web must also be ensured parallel to the actually desired leaktightness of the passage rims so that the treatment can be enabled. The air quantity to be sucked out initially for this purpose and the time required for this purpose are thereby increased and the detection reliability for the relevant film ruptures is lowered.

Figure 5A:
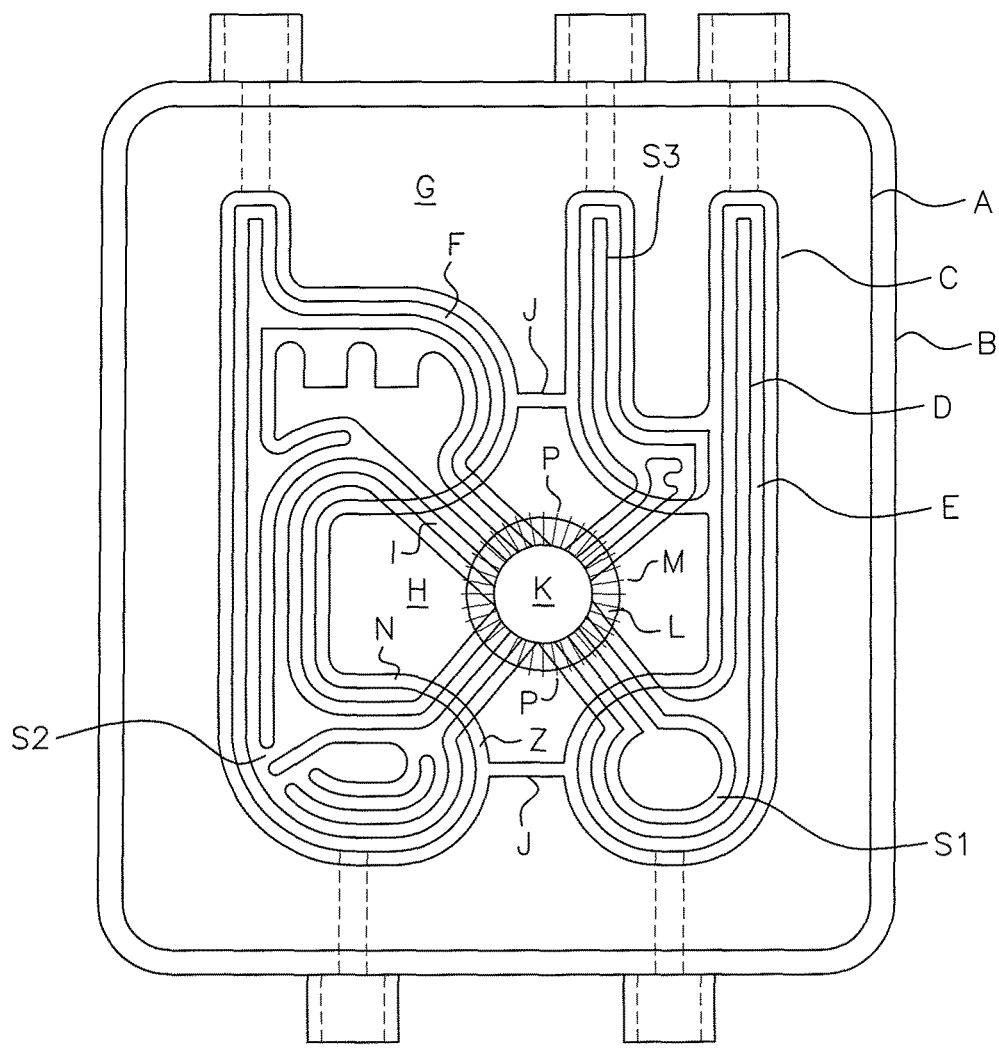
FIG. 5a: a plan view of a medical cassette in accordance with a fourth embodiment of the present invention.

A fourth embodiment of the present invention is therefore shown in FIG. 5*a* in which an internal structure of the structured surface of the film is used. Only the liquid-wetted film areas required from a technical process aspect are made capable of drainage in the internal structure. The pressing between the outer side of the film and the coupling plane is significantly lower than the pressing on the passage rim sealing webs and in the non-liquid areas G and H. In these latter areas, the cassette has flat sealing bases parallel to the film. Whereas the passage rim sealing webs are configured such that the liquid cannot overflow in the normal case, the areas G and H are configured such that liquid which has penetrated does not find any space since the pressing of the rubber mat effects an approximately full contact of the film both to the cassette plane and to the lowered rubber plane.

Since the pressing between the film and the rubber mat is significantly lower in the liquid-wetted internal areas S1, S2 and S3 than the pressing in all other areas of the film zone, a much less pronounced drainage structure is sufficient in this area both to ensure the complete film coupling and to ensure the complete detection of the relevant film surface with respect to possible ruptures. A safety spacing E of the structure D of approximately up to 1 mm can therefore be provided in the internal structure to the passage web edges C.

The areas G and H are covered by the sterilization process and hermetically sealed toward the outer world. If now a rupture nevertheless occurs in the region of the area G during the treatment, that is after an initial integrity test without findings, this as a rule remains without consequence for the treatment since the relevant areas S are not affected and since there is no possibility of the liquid entering into the area G. If a rupture occurs at a passage sealing web and beyond it, as sketched by F, the functions of the self-sealing come into effect due to the high pressings between the smooth film and the smooth rubber mat and furthermore due to the additional pressing on the peripheral rim. If a rupture occurs in the internal areas S during the treatment, the leak fluid penetrates into the space between the film and the rubber mat, further reduces the pressing and is finally pressed up to and onto the suction point K along the anisotropic structure D. Even the collection area H is only insignificantly filled with leak fluid in this context since the path over the direct conducting paths I to the suction point K offers the lowest flow resistance.

The internal structure provides less detection time and higher detection accuracy in the integrity test before the filling with treatment liquid. The internal structure provides redundant passive leak protection in the first defect case of the film rupture during treatment. The internal structure provides a much smaller area of the film and rubber mat which can be wetted on film rupture and which can, vice versa, contribute to the contamination of the treatment surface in the treatment liquid. The internal structure can increase the reliability and reduces the detection time of an occurring film rupture during the treatment and thus increases the security against contamination and cross-contamination. The internal structure can reduce the probability and the extent of possible liquid losses to the outside.

The possibility of an anisotropic structure furthermore results: An anisotropic film structure or an anisotropic design of interspersed drainage layers means designing the intensity, the direction, the functionality and the non-presence of the drainage effect locally differently. This includes the previously described internal structure with an unstructured marginal region toward the passage sealing webs.

The next possibility is the deliberate provision of separate structure areas S1 . . . S3 with a minimized number of crossings I of passage sealing web regions. I also shows how a minimum of volume has to be sucked out or wetted due to the optimized structure in the case of the initial test and in the case of a leak.

Figure 5B:
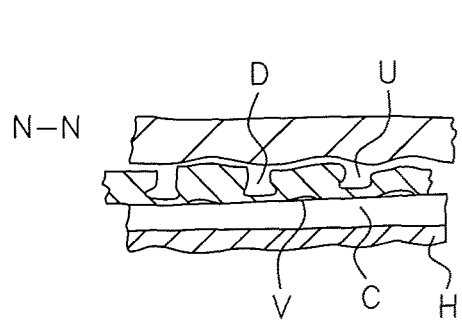
FIG. 5b: a sectional view through a structuring in a region with sealing webs.

The sectional representation FIG. 5*b* shows the optimized effect of linear structures which cross the passage rim sealing webs in perpendicular manner. An optimum of pressing leaktightness on the liquid side can be linked with an optimum obtaining of drainage structure depth on the machine side by this arrangement. The two basically negative designs of structures are shown with extreme exaggeration in the Figure, namely a partial squeezing closure U of the structure passages D and a pressing V interrupted by the inhomogeneous force conduction at the passage rim sealing webs C. Structures crossing the sealing webs in parallel or obliquely would penetrate further into the web and into the rubber mat and thus more greatly reduce the drainage effect and the pressing effect.

It must also be considered that it may be necessary at certain points, for example for the optical measurement of the liquid turbidity, or at passage points for ultrasound, that the film remains smooth and/or translucent. In this case, a window is provided by omission of structure or of drainage layers.

Possibilities furthermore result by the use of containment webs. If connection webs J are added between the passage rim sealing webs at suitable points of the passage and chamber layout, new areas H sealing pressed closed are obtained. If the drainage structures converge in this area, this area H forms the total area together with the liquid areas S1 ... S3 which is detected for film rupture before and during the treatment and which has a passively sealing pressed passage rim as an areal boundary for the conceivable leak fluid or for the conceivable contamination and cross-contamination. Each leak must finally reach this area H and this is the preferred location for suction points K with leak detectors and with hydrophobic contamination membranes.

Containment webs furthermore provide the possibility of somewhat reducing the pressing sealing effect at the points of the crossings I of the drainage structures over the passage sealing rims in favor of a better drainage effect (for example by a widening of the passage rim sealing webs) without outwardly reducing the effect of the reliable pressing leak-tightness.

The present invention furthermore provides the possibility of a non-invasive blood leak detection: The decision to cover the coupling plane of the machine with a closed protective layer, for instance of rubber, requires the consequence of also making a leak detector for the early discovery of film ruptures during the treatment as a device working in a non-invasive manner. This is, for example, possible through a thin rubber mat via capacitive sensors, via ultrasonic sensors or via the detection of the vacuum collapsing on a leak. This is possible via optical sensors with a reflection arrangement on the side of the mating coupling plane (to the nonfilm side of the cassette). A color sensor can, for example, distinguish in this context whether blood has exited or whether it is a normal moisture. The structure of the film can be utilized here to install a scattered light wetting detection. With a dry film, scattered light is reflected back at the structure which is absent if the structure is liquid-wetted. With such an arrangement on the non rubber mat side, the necessity for a sensor-sensitive special design of the rubber mat is therefore dispensed with.

Possibilities furthermore result due to specially structured weld seams and rubber mats: The problem in particular arises at the suction point K due to the annular weld seams required for this purpose around the hydrophobic membrane and around the hydrophobic membrane cut-out or the suction hole cut-out in the film that both a structure of the film and a welding on a drainage layer (for instance made of a nonwoven) disposed thereabove are leveled by an annular weld seam and thereby form annular barriers between the areas H and K.

Figure 5C:
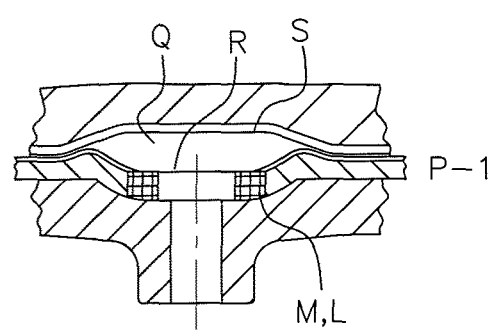
FIG. 5c: a sectional view through an embodiment of a suction opening in accordance with the invention.

To cancel these barrier possibilities, FIG. 5c shows a combination of four possible measures. A dent Q in the rubber mat equally reduces the sealing pressing against the annular weld seam as a dent R in the cassette surface. A further similar effect is achieved by the local structure S of the rubber mat in the region of the dent with grooves and patterns which radially bridge the weld seam at a plurality of points with a drainage effect.

The disadvantage of a worsened cleaning capability of the rubber mat results with both rubber mat measures. The counterpart to a structure of the rubber mat in the region of the suction point is a structure of the annular weld seam. For this purpose, the welding stamp is configured to be annular, but this ring is made more pronouncedly conically than the associated weld surface of the cassette. The annular surface M is furthermore equipped with radially arranged drainage ribs which leave a common structure of the cassette base and the film during welding, said common structure having a serrated annular surface with radially outwardly facing linear structures which extend up to and into the unwelded film regions after the welding due to the conical shape of the annular surface association, said linear structures form a total structure together with the radial structures already present there which is no longer interrupted by the annular sealing weld zone.

Figure 6:
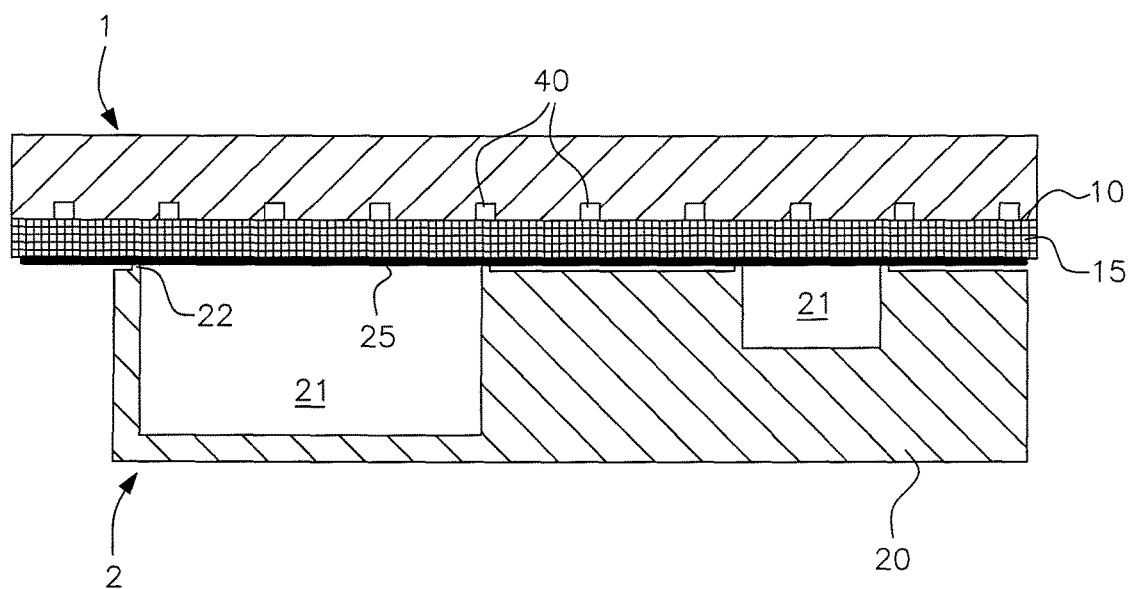
FIG. 6: an apparatus for treating a medical liquid in accordance with a fifth embodiment of the present invention.

FIG. 6 now shows a fifth embodiment of the apparatus for treating a medical liquid of the present invention in which the suction does not take place by an additional nonwoven between the flexible film 25 and the flexible mat 15 or by a corresponding structuring, but rather by the suitable choice of the mat material via the flexible mat 15 itself. For this purpose, the flexible mat comprises an air-permeable material (e.g. silicone) such that the air between the flexible mat 15 and the flexible film 25 can be sucked out directly through the mat 15 itself via the vacuum applied to the suction passages 40. The wide area distribution of the vacuum takes place in this context via the air passages 40 in the machine plate, whereas the permeable mat then permits an areal suction over the total surface. A complete closure of the suction is also practically precluded by this areal design.

In this embodiment, an already known medical cassette 2 made of a hard part 20 having liquid-conducting passages 21 can be used which is sealed by the flexible film 25. For this purpose, as in known systems, the medical cassette 2 is pressed with the flexible mat 15 of the treatment machine so that the sealing webs 22 provide a seal. In accordance with the invention, however, an areal suction is now possible which takes place via the vacuum passages 40 and via the permeable mat material on the machine side.

The mat material is advantageously air-permeable, but liquid-tight, in this context to avoid contamination of the coupling surface and to facilitate cleaning.

The possibility of determining leaks in the film moreover results by the possibility in accordance with the invention of sucking out air continuously between the flexible film 25 and the coupling surface 10. No vacuum can be built up after the pressing of the door in the case of a sufficiently large film leak due to the areal evacuation. Accordingly, air is constantly sucked out of the still unfilled disposable into the intermediate space between the film and the mat or the coupling surface. The too high leak rate can then be determined and registered via the vacuum monitoring and the vacuum evaluation. The check of the leaktightness can take place during and/or after the coupling to the cassette.

A leak in the disposable film can thus above all be recognized initially before the filling of the disposable and before starting treatment. The defective disposable can thereby be replaced by an intact one.

Without the areal suction, in contrast, such a check would be less reliable since a self-sealing can arise between the film and the mat and film leaks could still be present in regions with enclosed air islands, which leaks would not be detected via the vacuum monitoring and the vacuum evaluation. Basically, the check in accordance with the invention can, however, be carried out with any type of evacuation.

In this connection, the central idea of the invention is the areal suction of the air between the flexible film and the coupling surface, which is made possible by the different embodiments in that an air-permeable layer, a structuring of the surface of the flexible film and/or mat, a suction in the plane between the flexible mat and the flexible film and/or a suction through a permeable mat material is/are provided.

The invention being thus described, it will be apparent that the same may be varied in many ways. Such variations are not to be regarded as a departure form the spirit and scope of the invention, and all such modifications as would be recognized by one skilled in the art are intended to be included within the scope of the following claims.

What is claimed is:

1. An apparatus for treating a medical liquid comprising a treatment machine having a coupling surface, with a cassette made of a hard, part having liquid-conducting passages which are covered by a flexible film being able to be coupled to the coupling surface of the treatment machine, a surface of the flexible film facing the coupling surface of the treatment machine having a structuring, said structuring being formed by grooves that are recessed in the surface of the flexible film, the grooves forming passages through which air can be sucked out along the structuring of the film during the coupling process and/or with a coupled cassette.

2. An apparatus for treating a medical liquid comprising a treatment machine having a coupling surface and a flexible mat arranged on the coupling surface, with a cassette made of a hard part having liquid-conducting passages which are covered by a flexible film being able to be coupled to the coupling surface of the treatment machine via the flexible mat, a surface of the flexible mat facing the flexible film having a structuring, said structuring being formed by grooves that are recessed in the surface of the flexible mat, the grooves forming passages through which air can be sucked out along the structuring of the flexible mat during the coupling process and/or with a coupled cassette.

3. The apparatus in accordance with claim 1, wherein the structuring has a net structure and/or a meander-like and/or linear structure.

4. The apparatus in accordance with claim 1, wherein the structuring is made anisotropoic and/or inhomogeneous.

5. The apparatus in accordance with claim 1, wherein the structuring extends along the liquid-conducting passages.

6. The apparatus in accordance with claim 5, wherein the structuring converges in one or more regions outside the liquid-conducting passages which form suction points.

7. The apparatus in accordance with claim 1, wherein the structuring extends substantially perpendicular to a passage web edge on a transition from a-region with liquid-conducting passages to a region outside the liquid-conducting passages.

8. The apparatus in accordance with claim 5, wherein the structuring has a spacing from the passage web edges in the regions in which it does not traverse the passage web edges.

9. The apparatus in accordance with claim 5, wherein the structuring is made such, that there is no direct connection between regions of the film with different liquid-conducting passages.

10. The apparatus in accordance with claim 1, wherein the cassette is pressed with the coupling surface in the coupled state, with the film being pressed in a fluid-tight manner with the liquid-conducting passages of the hard part of the cassette, but with the structuring along its plane allowing air transport.

11. The apparatus in accordance with claim 1, wherein the apparatus includes at least one suction device.

12. The apparatus in accordance with claim 11, wherein the structuring is in communication with a vacuum device at one or more points outside the region of the liquid-conducting passages.

13. The apparatus in accordance with claim 1, wherein suction takes place via at least one valve arranged in the coupling surface of the treatment machine.

14. The apparatus in accordance with claim 1, wherein suction takes place via one ore more suction openings arranged in the hard part of the cassette.

15. The apparatus in accordance with claim 1, wherein the apparatus includes an optical sensor for the recognition of leaks.

16. The apparatus in accordance with claim 1, wherein the apparatus includes a vacuum device that carries out an automatic suction of the air.

17. The apparatus in accordance with claim 16, wherein the vacuum device carries out an automatic check of the leaktightness of the cassette.

18. A medical cassette made of a hard part having liquid-conducting passages which are covered by a flexible film, with the cassette be able to be coupled to a coupling surface of a treatment machine, a surface of the flexible film facing the coupling surface of the treatment machine having a structuring, said structuring being formed by grooves that are recessed in the surface of the flexible film, the grooves forming passages through which air can be sucked out along the plane of the film in the coupled state of the cassette.

19. The medical cassette in accordance with claim 18, wherein the hard part of the cassette has a peripheral marginal region into which the structuring does not extend so that this marginal region forms a sealing web on pressing.

20. The medical cassette in accordance with claim 19, wherein the flexible film is welded to the hard part of the cassette in the peripheral marginal region.

21. The medical cassette in accordance with claim 18, wherein the structuring has a net structure and/or a meander-like structure and/or a linear structure.

22. The medical cassette in accordance with claim 18, wherein the structuring is made anisotropic and/or inhomogeneous.

23. The medical cassette in accordance with claim 18, wherein the structuring extends along the liquid-conducting passages.

24. The medical cassette in accordance with claim 18, wherein the structuring converges in one or more regions outside the liquid-conducting passages which form suction points.

25. The medical cassette in accordance with claim 18, wherein the structuring extends substantially perpendicular to a passage web edge on a transition from a region with liquid-conducting passages to a region outside the liquid-conducting passages.

26. The medical cassette in accordance with claim 23, wherein the structuring has a spacing from the passage web edges in the regions in which it does not traverse the passage web edges.

27. The medical cassette in accordance with claim 23, wherein the structuring is made such that there is no direct connection between regions of the film with different liquid-conducting passages.

28. The medical cassette in accordance with claim 18, wherein the hard part has containment webs which connect passage rim sealing webs and form areas sealing pressed closed.

29. The medical cassette in accordance with claim 18, the cassette includes at least one suction opening arranged in the hard part of the cassette.

30. The medical cassette in accordance with claim 29, wherein the suction opening is arranged outside the region of the liquid-conducting passages.

31. The medical cassette in accordance with claim 29, wherein the flexible film is welded to the hard part of the cassette around the suction opening by an annular weld seam.

32. The medical cassette in accordance with claim 31, wherein the annular weld seam has a structuring around the suction opening.

33. The medical cassette in accordance with claim 31, wherein a region including the weld seam is lowered with respect to a pressing plane of the cassette.

34. The medical cassette in accordance with claim 29, wherein a hydrophobic filter is arranged at the suction opening.

35. A method for coupling a medical cassette made of a hard part having liquid-conducting passages which are covered by a flexible film to a coupling surface of a treatment machine for treating a medical fluid comprising the steps:
coupling the medical cassette to the coupling surface of the treatment machine;
suctioning of air between the flexible film and the coupling surface of the treatment machine during the coupling process and/or with a coupled cassette, said suctioning of air taking place along a structuring of a surface of the flexible film that faces the coupling surface of the treatment machine, structuring being formed by grooves that are recessed in the surface of the flexible film, the grooves forming passages for suction of air and/or along a structuring of a surface of a flexible mat facing the flexible film, said structuring being formed by grooves that are recessed in the surface of the flexible mat, the grooves forming passages for suction of air.

* * * * *